United States Patent
Mittelstaedt et al.

(10) Patent No.: US 6,268,492 B1
(45) Date of Patent: Jul. 31, 2001

(54) METHODS FOR PURIFYING NON-CHROMOSOMAL NUCLEIC ACID MOLECULES FROM CELLS

(75) Inventors: Denice M. Mittelstaedt; David Chi-Tang Hsu, both of San Diego County, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/363,209

(22) Filed: Jul. 29, 1999

Related U.S. Application Data
(60) Provisional application No. 60/096,009, filed on Aug. 10, 1998.

(51) Int. Cl.[7] .......................... C07H 21/00; C07H 23/00
(52) U.S. Cl. ........................................ 536/25.4; 536/26.43
(58) Field of Search ........................ 536/25.4, 26.52, 536/26.43; 424/124; 435/384, 404

(56) References Cited

U.S. PATENT DOCUMENTS
| | | |
|---|---|---|
| 5,576,196 | 11/1996 | Horn et al. |
| 5,645,986 | 7/1997 | West et al. |
| 5,981,735 * | 11/1999 | Thatcher et al. .................. 536/25.4 |

FOREIGN PATENT DOCUMENTS
| | | |
|---|---|---|
| WO 93/11218 | 6/1993 | (WO). |
| WO 96/02658 | 2/1996 | (WO). |
| WO 97/29190 | 8/1997 | (WO). |
| WO9805673 * | 2/1998 | (WO). |

OTHER PUBLICATIONS

Lacoste–Bourgeacq et al., "A New Procedure Using Membrane Chromatography for the Valorization of Fraction IV from Kistler and Nitschmann's Fractionation of Blood Plasma", Chromatographia, 1991, vol. 32, No. 1–2, pp. 27–32.*

Van Reis et al., "Industrial Scale Harvest of Proteins from Mammalian Cell Culture by Tangential Flow Filtration; Protein Purification ...", Biotechnology and Bioengineering, 1991, vol. 38, No. 4, pp. 413–422.*

Scawen et al., "Protein Recovery; Large–scale enzyme isolation and purification methods", Bioactive Microbial Products 3: Downstream Process, 1986, pp. 77–101.*

Brasch et al, "Isolation and Analysis of Nuclear Bodies from Estrogen–Stimulated Chick Liver", Experimental Cell Research, 1989, vol. 182, No. 2, pp. 425–435.*

* cited by examiner

Primary Examiner—John S. Brusca
Assistant Examiner—Young Kim
(74) Attorney, Agent, or Firm—Anne S. Dollard; David D. McMasters; Robert P. Blackburn

(57) ABSTRACT

Methods are provided for purifying non-chromosomal nucleic acid molecules from cells, comprising: the general steps of (a) lysing cells to form a nucleic acid-containing lysate, and (b) applying the lysate to a depth filter in order to obtain a clarified solution containing purified non-chromosomal nucleic acid molecules.

14 Claims, 2 Drawing Sheets

METHODS FOR PURIFYING NON-CHROMOSOMAL NUCLEIC ACID MOLECULES FROM CELLS

CROSS-REFERENCE TO RELATED APPLICATIONS

This application claims the benefit of U.S. Provisional Application No. 60/096,009, filed Aug. 10, 1998.

TECHNICAL FIELD

The present invention relates generally to biotechnology, and more specifically, to a method for purifying non-chromosomal nucleic acid molecules from a cell lysate.

BACKGROUND OF THE INVENTION

Since the discovery of the structure of nucleic acid molecules (DNA and RNA) in the 1950's, research into the structure, function, and use of these molecules has increased dramatically. In particular, a tremendous amount of research has been undertaken in order to utilize these molecules to diagnose and treat disease. In order however to obtain sufficient quantities of nucleic acids for use in experiments, and for diagnosis and treatment of disease, it is first necessary to purify and or isolate substantial quantities of nucleic acid molecules. For example, in the field of gene therapy, patients can be vaccinated or treated with nucleic acid molecules in order to protect against, or, remedy a disease (see, e.g., PCT publication WO 95/07994). However, preparation of large-quantities of purified, pharmaceutical-grade nucleic acid molecules is presently time-consuming and costly.

More specifically, while many methods exist for the purification of nucleic acid molecules, such methods are often limited when the nucleic acid molecules are to be produced for therapeutic purposes, since they must be prepared free of any contaminants such as toxic compounds and antigenic molecules. Prior art methods of DNA purification often utilized highly toxic chemicals such as ethidium bromide, phenol, chloroform, and cesium chloride (Sambrook, et al., 1992, Molecular Cloning: A Laboratory Manual (2nd ed.), Cold Spring Harbor, N.Y.). Additionally, many methods involving both physical or chemical lysis often relied upon centrifugation to remove cellular debris, a step which is undesirable because of the difficulty in maintaining sterility. Furthermore, procedures using alkali lysis (Bimboim and Doly, Nucleic Acids Res. 7;1513, 1979) may lead to the loss of a significant amount of DNA through degradation caused by the increase in pH.

The present invention provides methods for producing purified nucleic acid molecules that are suitable for use in pharmaceutical applications, and on a large scale. Such methods do not require traditional techniques such as toxic extractants, mutagenic reagents, or steps such as centifugation. The present invention also provides other, related advantages.

SUMMARY OF THE INVENTION

Briefly stated, the present invention provides methods for purifying non-chromosomal nucleic acid molecules from cells, comprising the general steps of (a) lysing cells to form a nucleic acid-molecule containing lysate, (b) precipitating chromosomal DNA and cell wall components from the lysate, in order to form a flocculent solution, and (c) applying the flocculent solution to a depth filter, such that non-chromosomal nucleic acid molecules are purified.

Within further embodiments, the non-chromosomal nucleic acid molecules can be further isolated by chromatographically separating non-chromosomal nucleic acid molecules (e.g., by ion-exchange chromatography or preparative HPLC) from proteins and other compounds which are in the lysate. Within other embodiments, the clarified solution may be concentrated (e.g., by centrifugation or tangential flow). Within yet other embodiments the purification and/or isolation methods described herein can be performed in a sterile environment and/or in a continuous manner.

The methods provided herein may be utilized to purify and/or isolate a variety of non-chromosomal nucleic acid molecules, including for example plasmids and RNA.

Within certain embodiments of the invention, the depth filter has a nominal pore size of between about 0.2 and 20 microns. Within other embodiments, the non-chromosomal nucleic acid molecules are precipitated utilizing a neutralizing agent such as sodium acetate or potassium acetate.

The methods provided herein may be utilized for purifying and/or isolating non-chromosomal nucleic acid molecules from a wide variety of cells, including for example, bacterial cells, yeast cells, and mammalian cells (i.e., both eukaryotic and prokaryotic cells).

These and other aspects of the present invention will become evident upon reference to the following detailed description and attached drawings. In addition, various references are set forth herein which describe in more detail certain procedures or compositions (e.g., plasmids, etc.), and are therefore incorporated by reference in their entirety.

DETAILED DESCRIPTION OF THE INVENTION

Definitions

Figure 1:
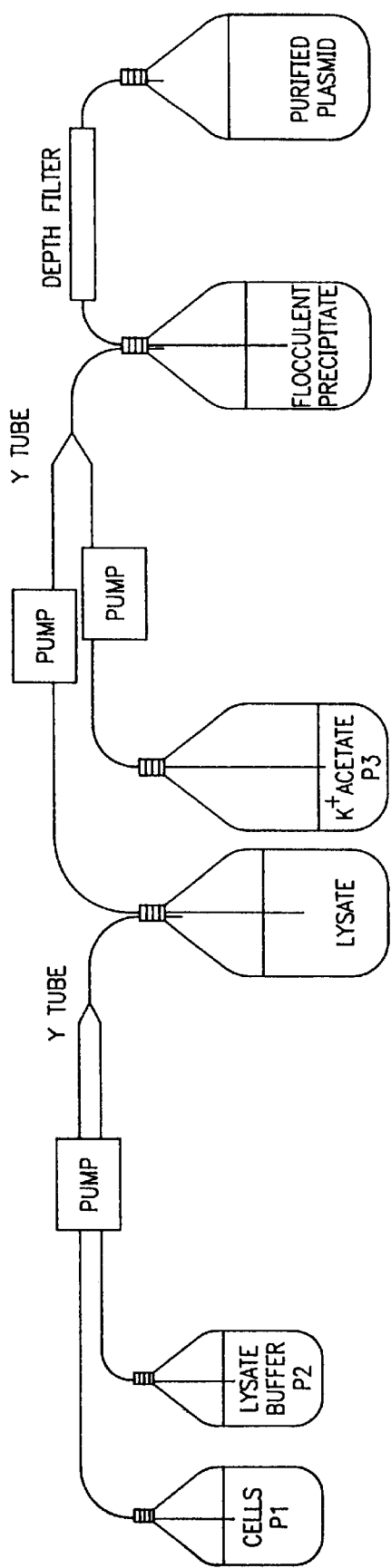
FIG. 1 is a schematic illustration of one representative purification method of the present invention.
Figure 2:
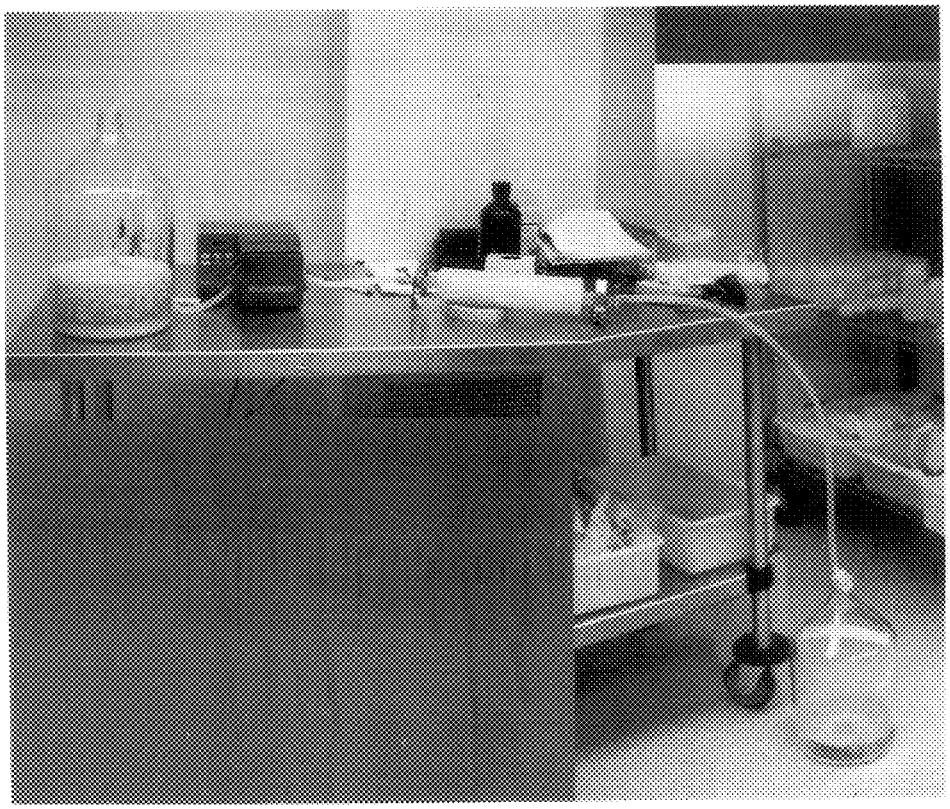
FIG. 2 is a photograph which shows the removal of precipitated debris.

Prior to setting forth the invention, it may be helpful to an understanding thereof to first set forth definitions of certain terms that will be used hereinafter.

"Depth filter" refers to a filter which is capable excluding particles of a selected size from a given media. Depth filters, (as opposed to membrane filters) exclude particles from media by capturing particles within the matrix of the media (as compared to primarily the surface of the media for membrane filters). Depth filters are typically composed of fibrous media, usually cellulose, glass fiber, or, polypropylene (or a combination of these).

"Purified" non-chromosomal nucleic acid molecules, as utilized within the context of the present invention, refers to nucleic acid molecules that are substantially free of cellular debris and chromosomal DNA (i.e., has an absorbance of 0.010 as determined by spectrophotometric analysis at 600 nm, and preferably less than 0.005, 0.002, or, 0.001).

"Isolated" non-chromosomal nucleic acid molecules, as utilized within the context of the present invention, refers to a preparation of nucleic acid molecules which, when linearized and applied to an agarose gel, upon application of an appropriate voltage form a single broad band of nucleic acid molecules. If the nucleic acid molecules are not linearized, a broad band or 3 separate close bands of supercoiled (dimers or oligomers), relaxed and/or linear nucleic acids are obtained. Protein assays can also be performed in order to ensure that the protein content is less than 10 ug/ml, and preferably less than 5, 2, or 1 ug/ml.

As noted above, the present invention provides methods for purifying non-chromosomal nucleic acid molecules from cells, comprising the general steps of (a) lysing cells to form a nucleic acid-molecule containing lysate, (b) precipitating chromosomal DNA and cell wall components from the lysate, in order to form a flocculent solution, and (c) applying the flocculent solution to a depth filter, such that non-chromosomal nucleic acid molecules are purified. Briefly, by utilizing a depth filter for removing cellular debris and other precipitates that are formed due to the lysing of cells, one can readily purify non-chromosomal nucleic acid molecules without the need for traditional separation steps such as centrifugation, or filtration through membrane filters such as Watman paper, or, cheesecloth. Such methods may be readily accomplished without the use of polyethylene glycol, or organic extractants (e.g., phenol or ethidium bromide).

In order to further the understanding of the invention, set forth below is a brief discussion of methods for lysing cells, precipitating chromosomal DNA and cell wall components, and filtering the resultant flocculent solution. Furthermore, methods are provided for further isolating and/or concentrating the purified non-chromosomal nucleic acid molecules. Also, a discussion is provided on the use of these non-chromosomal molecules in research and pharmaceutical applications.

Lysing Cells

Utilizing the methods of the present invention, non-chromosomal nucleic acid molecules can be purified from a wide variety of cells, including for example both mammalian (e.g., human, rat and mouse) and non-mammalian (e.g., bacterial, yeast, or insect) cells. Briefly, the first step is to lyse the cells in order to form a lysate containing cytoplasmic proteins and plasmids. A wide variety of methods can be utilized to lyse cells, including for example, physical methods such as homogenization, sonication or the use of a French Press, and chemical (e.g., chemical lysis) and enzymatic methods (e.g., lysozyme).

Briefly, in order to homogenize cells, cellular material is first blended with a mortar and pestle or a blender. Typically for purification of non-chromosomal nucleic acid molecules from bacteria, a bacterial pellet is resuspended into a solution and a mortar and pestle or blender is utilized to rupture cell walls. One alternative method of homogenization is the French Press. Briefly, within such a press a cell pellet is suspended in solution and squeezed between two hard surfaces. Once the cell wall is ruptured, cellular components containing cytoplasmic proteins and plasmids are released.

In order to sonicate cells, cells are placed in a sonication bath, or alternatively, a probe-type oscillator is placed into a vessel containing the cells. Representative examples of suitable sonciators include the SonifierII® Cell Disrupter (Branson), or, the Ultrasonic Cleaner (Branson).

Chemical lysis may readily be accomplished by a variety of methods. For example, within one embodiment a bacterial pellet is suspended in buffer. The solution is rapidly and completely mixed with 0.2M NaOH and 1% SDS (or equivalent). This is allowed to incubate for a maximum of five minutes. The solution is then neutralized with either potassium or sodium acetate. This forms a precipitate consisting of cellular debris and genomic DNA. It is also possible during this step to introduce RNase A for reduction of free RNA.

Cells may also be lysed by enzymatic means utilizing commonly available enzymes such as lysozyme.

Any of the above procedures can be utilized to lyse cells in order to form a lysate containing cytoplasmic proteins and plasmids. Briefly, these processes result in the protein or plasmid being released from the cell primarily causing large holes in the cell wall. The cellular debris and chromosomal DNA trapped within the cell form a precipitate. Separation of this precipitate can occur by different methods dependent on the material required.

Preciptating a Lysate From a Flocculent Solution

A wide variety of methods may be utilized to precipitate a lysate (e.g., cellular debris and chromosomal DNA) from a flocculent solution, including for example, chemically (e.g., by pH change or the addition of salt), or physically (e.g., by the use of heat). As an illustration, during chemical lysis, high pH of the lysate can be achieved by the addition of sodium hydroxide to the lysis buffer, followed by sodium acetate or potassium acetate to neutralize the lysate, and to cause precipitation of cellular debris and chromosomal DNA. If homogenization is utilized to lyse cells, either streptomycin sulfate or ammonium sulfate may be utilized to precipitate the lysate.

Utilizing the methods provided herein, at least 5 to 6 liters of flocculent solution may be processed utilizing just one filter with ten square feet of surface area. In order to scale up the processing of fluids, multiple filters may be added in order to process in parallel (or, alternatively, serially) larger volumes of fluids.

Filtering a Lysate

As noted above, once a flocculent solution has been generated, the solution is applied to a depth filter. As noted above, the term 'depth filter' refers to a filter which are capable excluding particles of a selected size from a given media. Depth filters, (as opposed to membrane filters) exclude particles from media by capturing particles within the matrix of the media (as compared to primarily the surface of the media for membrane filters).

Depth filters are typically composed of fibrous media, usually cellulose, glass fiber, or, polypropylene (or a combination of these). Depth filters suitable for use within the present invention may be purchased commercially, at, for example, Sartorius Corporation (Edgewood, N.Y.), Millipore, of Gillman. Depth filters are also described within U.S. Pat. No. 4,594,202 (Method of Making Cylindrical Fibrous filter Structures"), U.S. Pat. No. 4,726,901 (entitled "Cylindrical Fibrous Structures With Graded Pore Size"), and EPO 0148638 entitled "Cylindrical Fibrous Structures and Method of Manufacture").

Utilizing such techniques, non-chromosomal nucleic acid molecules can be readily purified from at least 10, 15, or even 25 grams (wet weight) per liter of cells, at a substantially faster rate than conventional methods. Moreover, the process described herein is scalable, allowing 1, 2, 3, 4, 5 liters (or even greater quantities) of cells to be lysed and filtered for non-chromosomal nucleic acid molecules. For example, 125 grams of cells (wet weight) in 5 liters can be filitered using a depth filter with 5–10 square feet of surface area.

Isolating and/or Concentrating Non-Chromosomal Nucleic Acid Molecules

After the flocculent solution is applied to a depth filter, the resultant solution containing purified non-chromosomal nucleic acid molecules may, optionally, be applied to further process steps in order to isolate and or further concentrate the non-chromosomal nucleic acid molecules.

For example, utilizing chromatographic techniques, (e.g., ion exchange and/or size exclusion) one can readily isolate the non-chromosomal nucleic acid molecules. Briefly, ion exchange utilizes anion columns including either DEAE or Q resins. Qiagen, Santa Clarita has a patent for use of DEAE resin in plasmid purification while the primary Q resin patent for use in plasmid DNA is by Biosepra, Boston. Experiments with alternative resins have shown consistency in the results. There is also an affinity resin available from Puresyn, Boston that can be used after ion exchange. Typically the concentration of the plasmid DNA following chromatography is dilute.

Concentration of the purified and/or isolated non-chromosomal nucleic acids may also be accomplished utilizing techniques such as precipitation and Tangential Flow Filtration.

Briefly, precipitation usually involves the addition of an alcohol (e.g., isopropanol or ethanol) to the solution followed by centrifugation. The plasmid DNA forms a pellet that is then rinsed with ethanol and allowed to air dry. The plasmid DNA can then be dissolved into any buffer.

Tangential flow filtration can be used by limiting the cut-off size and both reducing the volume, removing small particle contaminants and acting as a buffer exchange. With Tangential Flow Filtration, the cut-off size required is much smaller than expected due to the compact properties of supercoiled plasmid.

Methods for Utilizing Purified or Isolated Nucleic Acid, and Pharmaceutical Compositions Purified or isolated nucleic acid molecules of the present invention have a variety of uses. For example, within one embodiment of the invention the isolated nucleic acid molecules may be utilized for diagnostic assays, or, alternatively, for therapeutic purposes.

When utilized for therapeutic purpose, the purified and/or isolated nucleic acid molecules may be further formulated with one or more excipients, buffers or stabilizers. In addition, the nucleic acid molecules will typically be provided in a sterile, pyrogen-free form, in a suitable dosage for administration for the intended purposes.

Representative examples of such therapeutic techniques and methods are provided in PCT Publication Nos. WO 95/07994 and WO 96/40952 and U.S. Pat. Nos. 5,580,859 and 5,589,466.

The following examples are offered by way of illustration, and not by way of limitation.

EXAMPLES

Example 1

Purification of Plasmid DNA From *E. COLI* DH5-α Cells

This example demonstrates a method of purifying plasmids from *E. coli* DH5-α cells. Briefly, from *E. coli* DH5-α cells containing the ELVS 1.5 β-gal plasmid (see WO 97/38087) were grown in Digene superbroth with phosphate (Digene, Beltsville, Md.) containing the antibiotic kanamycin (50 mg/ml, Sigma, St. Louis, Mo.). The cells were incubated for 20–28 hours at 37° C. in a shaker bath. The cells were then harvested by centrifugation at 5000×G) for 15 minutes at 2–10° C. The supernatant was discarded and the pellets were resuspended in 2 liters of P1-RNase-A buffer (50 mM Tris/HCl, 10 mM EDTA, pH 8.0, containing 100 mg RNase-A per liter, Qiagen, Santa Clarita, Calif.). The cells were then lysed upon addition of 2.15 liters of lysis buffer P2 (200 mM NaOH, 1% SDS, Qiagen, Santa Clarita, Calif.). This was accomplished by allowing the resuspended cells to come in contact with the lysis buffer through a "Y" connector tube which connected 3 pieces of tubing (see FIG. 1). This method of mixing does not require inversion. A dual head peristaltic pump was used to generate the flow of the fluids.

P3 buffer containing 3.0 M potassium acetate pH 5.5 (Qiagen, Santa Clarita, Calif.) was added to the above lysed cells through a similar type of "Y" connector tube, except that a second pump was used to simultaneously regulate the flow at an approximate 2:1 ratio of lysate to P3 buffer. This solution formed a precipitate and was allowed to incubate on ice for a minimum of 30 minutes.

The precipitated solution was pumped directly through a Sartopure PP2 0.5 m depth filter capsule (Sartorius, Inc., Yauca, P. R.). Endotoxin was removed by adding Endotoxin Removal (ER) Buffer (Qiagen, Santa Clarita, Calif.) to the filtered pool and mixing uniformly.

Following incubation for a minimum of 1 hour on ice, the combined ER buffer and filtered lysate pool was transferred to the chromatography unit, an ion exchange column (Ultrapure 100, Qiagen, Santa Clarita, Calif.). The run cycle was set at a flow rate of 5 mL/min. for 18 hours prior to washing with QC buffer (1 M NaCl, 50 mM MOPS, 15% Ethanol, pH 7.0) at a flow rate of 20 ml/min for 2½ hours. The plasmids were eluted with QN buffer (1.6 M NaCL, 50 mM MOPS, 15% Ethanol, pH 7.0). The plasmids were then precipitated with isopropanol to a final concentration of 42%, centrifuged for 60 minutes at 13,000×G at 2–8° C., washed with 70% ethanol, and resuspended in TE (10 mM TRIS-HCl, 1 mM EDTA). Upon subsequent, analysis utilizing a Pierce Protein Microassay, less than 1.25 ug/ml protein was detected.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for purifying non-chromosomal nucleic acid molecules from cells, comprising:
    a) lysing cells to form a nucleic acid molecule-containing lysate;
    b) precipitating chromosomal DNA and cell wall components from the lysate, in order to form a flocculent solution; and
    c) applying the flocculent solution to a depth filter to capture said precipitated chromosomal DNA and cell wall components within said depth filter and to allow non-chromosomal nucleic acid molecules to pass through said depth filter, such that said non-chromosomal nucleic acid molecules are purified, with the proviso that said flocculent solution is not centrifuged prior to applying the solution to said depth filter.

2. The method according to claim 1 wherein the step of lysing is accomplished by homogenizing cells.

3. The method according to claim 1 wherein the step of lysing is accomplished by chemical lysis.

4. The method according to claim 1, further comprising the step of chromatographically isolating said purified non-chromosomal nucleic acid molecules.

5. The method according to claim 4 wherein said purified non-chromosomal nucleic acid molecules are separated on an ion-exchange column.

6. The method according to claim 1, further comprising the step of concentrating said purified non-chromosomal nucleic acid molecules.

7. The method according to claim 4 wherein said purified non-chromosomal nucleic acid molecules are concentrated by tangential flow.

8. The method according to claim 1 wherein said non-chromosomal nucleic acid molecules are plasmids.

9. The method according to claim 1 wherein said non-chromosomal nucleic acid molecules are RNA.

10. The method according to claim 1 wherein said depth filter has a nominal pore size of between 0.2 and 20 microns.

11. The method according to claim 1 wherein any one of steps a) through c) are performed in a sterile environment.

12. The method according to claim 1 wherein any one of steps a) through c) are performed in a continuous manner.

13. The method according to claim 1 wherein said cells are bacteria.

14. The method according to claim 1 wherein said cells are eukaryotic cells.

* * * * *